United States Patent [19]
Chan et al.

[11] Patent Number: 6,103,295
[45] Date of Patent: Aug. 15, 2000

[54] METHOD OF AFFIXING RADIOISOTOPES ONTO THE SURFACE OF A DEVICE

[75] Inventors: Albert Chan, Ottawa; Stephen M. Oelsner, White Lake; Thomas J. Simpson, Nepean, all of Canada

[73] Assignee: MDS Nordion Inc., Ontario, Canada

[21] Appl. No.: 08/995,524

[22] Filed: Dec. 22, 1997

[51] Int. Cl.$^7$ .................. A61M 36/14; A61M 36/00; B05D 1/18; B05D 3/02
[52] U.S. Cl. .................. 427/5; 427/346; 427/383.1; 427/436; 427/443.2; 427/601
[58] Field of Search .................. 427/5, 6, 346, 427/347, 383.1, 376.1, 443.2, 435, 436

[56] References Cited

U.S. PATENT DOCUMENTS

| | | | |
|---|---|---|---|
| 2,711,484 | 6/1955 | Knapp, Jr. et al. .................. | 250/83.6 |
| 3,582,656 | 6/1971 | Koehler .................. | 250/83.3 |
| 3,769,511 | 10/1973 | Delacy .................. | 250/303 |
| 3,974,322 | 8/1976 | Drabkina et al. .................. | 428/433 |
| 4,169,186 | 9/1979 | Tazaki et al. .................. | 428/406 |
| 4,702,228 | 10/1987 | Russell, Jr. et al. . | |
| 4,815,449 | 3/1989 | Horowitz . | |
| 4,818,307 | 4/1989 | Mori et al. .................. | 148/414 |
| 4,900,368 | 2/1990 | Brotz .................. | 136/253 |
| 4,994,013 | 2/1991 | Suthanthiran et al. . | |
| 5,059,166 | 10/1991 | Fischell et al. . | |
| 5,163,896 | 11/1992 | Suthanthiran et al. . | |
| 5,176,617 | 1/1993 | Fischell et al. . | |
| 5,197,940 | 3/1993 | Sievert et al. .................. | 600/9 |
| 5,213,561 | 5/1993 | Weinstein et al. . | |
| 5,342,283 | 8/1994 | Good . | |
| 5,405,309 | 4/1995 | Carden, Jr. . | |
| 5,479,969 | 1/1996 | Hardie et al. .................. | 141/130 |
| 5,484,384 | 1/1996 | Fearnot . | |
| 5,498,227 | 3/1996 | Mawad . | |
| 5,575,749 | 11/1996 | Liprie . | |
| 5,618,266 | 4/1997 | LIprie . | |
| 5,707,332 | 1/1998 | Weinberger .................. | 600/3 |

FOREIGN PATENT DOCUMENTS

WO 93/04735  3/1993  WIPO .

OTHER PUBLICATIONS

Eichholz et al., "Adsorption of Ions in Dilute Aqueous Solution on Glass and Plastic Surfaces", Analytical Chemistry, vol. 37, No. 7, pp. 863–868, Jun. 1965.

Madigan et al, Sonochemical Stripping Voltammetry, Anal. Chem. 1995, 67, 2781–2786.

Wizemann et al, Cancellation of Matrix Effects and Calibration by Isotope Dilution in Isotope–Selective Diode Laser Atomic Absorption Spectrometry, Anal. Chem. 1997, 69, 4291–4293.

Arlinghaus et al, Multiplexed DNA Sequencing and Diagnostics by Hybridization with Enriched Stable Isotope Labels, Anal. Chem. 1997, 69, 1510–1517.

Fehsenfeld et al, Radionuclide Technique in Mechanical Engineering in Germany, Journal of Radioanalytical and Nuclear Chemistry: Articles, vol. 160, No. 1 (1992) 141–151.

Eichholz et al, Adsorption of Ions in Dilute Aqueous Solutions on Glass and Plastic Surfaces, vol. 37, No. 7, Jun., 1965, 863–868.

(List continued on next page.)

*Primary Examiner*—Shrive Beck
*Assistant Examiner*—Michael Barr
*Attorney, Agent, or Firm*—Sughrue, Mion, Zinn, Macpeak & Seas, PLLC

[57] ABSTRACT

A method for coating a substrate with a radioisotope comprising is disclosed. The method comprises immersing the substrate within a solution containing a $\gamma$, $\beta^+$, $\alpha$ or $\beta^-$ emitting radioisotope, then exposing the immersed substrate to tuned vibrational cavitation (i.e. ultrasonic) to produce a coated substrate, followed by baking the coated substrate at a temperature below the recrystallization temperature of the substrate. Following this step, the substrate is rinsed and dried. Substrates coated using the method of this invention exhibit very low rates of leaching of the coated radioisotope, and are suitable for use within medical applications.

28 Claims, 11 Drawing Sheets

OTHER PUBLICATIONS

Wong et a, Intracoronary stents, Current Opinion in Cardiology, 1995, 10:404–411.

Carter et al, Effects of Endovascular Radiation From a β–Particle–Emitting Stent in a Porcine Coronary Restenosis Model, Circulation 94:2364–68 (1996).

Fischell et al, The Beta–Particle–Emitting Radioisotope Stents (Isostent): Animal Studies and Planned Clinical Trials, The American Journal of Cardiology, vol. 78 (3A) 1996, 45–50.

Hehrlein et al, Low–Dose Radioactive Endovascular Stents Prevent Smooth Muscle Cell Proliferation and Neointimal Hyperplasia in Rabbits, Circulation 92: 1570–75, 1995.

Violaris et al, Endovascular stents: a 'break through technology', future challenges, International Journal of Cardiac Imaging 13:3–13, 1997.

Prestwich, Analytic representation of the dose from a $^{32}$P–coated stent, Med. Phys. 23(1) Jan., 1996 9–13.

Janicki et al, Radiation dose from a phosphorous–32 impregnated wire mesh vascular stent, Med. Phys. 24(3) 1997—437–445.

METHOD OF AFFIXING RADIOISOTOPES ONTO THE SURFACE OF A DEVICE

The present invention relates to a method of producing a uniform distribution of radioisotope on a surface of a device. Furthermore, this invention is directed to coated products prepared using the disclosed method. More specifically, this invention is directed at permanently affixing a radioisotope of interest on the surface of a medical device.

BACKGROUND OF THE INVENTION

In recent years the treatment of medical ailments using implantable devices treated with radioactivity has gained prominence throughout the medical community. This is because the antiproliferative effect of ionizing radiation has been recognized, and used, to reduce proliferative cell growth including, cancer cell growth. An advantage of using radioactive devices to apply the radiotherapy treatment is that the dose of radioactivity is localized and minimizes the total overall dose given to the patient. For example, it has been proposed that over 95% of the radiation dose is delivered within 5–6 mm of the implantation site (Fischell et al 1996, which is incorporated by reference). Typical applications of medical devices, treated so that they are radioactive, include the treatment of localized lesions using radioactive implants, stents and/or brachytherapy wires, or for example, the treatment of aberrant cell growth using radioactively treated catheters, or catheters capable of accepting radioactive inserts (U.S. Pat. No. 5,213,561; U.S. Pat. No. 5,484,384; U.S. Pat. No. 5,498,227; U.S. Pat. No. 5,575,749; WO 93/04735; Violaris et al 1997; Carter et al 1996; Fischell et al 1996; Hehrlein et al 1995, Wong and Leon 1995, which are all incorporated by reference). Other medical devices that are useful in treatment of cancers and the like include implantable radioactive sources, such as seeds etc (U.S. Pat. No. 4,815,449; U.S. Pat. No. 4,994,013; U.S. Pat. No. 5,342,283; U.S. Pat. No. 5,405,309, which are incorporated by reference).

Several important criteria for a radioactively treated medical device have been identified. It is generally desired within the art that medical devices treated with radioactivity exhibit a uniform, homogeneous distribution of radioisotope over the length and breadth of the device, and that the radioisotope be permanently affixed to the device and not leach out and contaminate the surrounding tissues when the device is implanted. The production of radioactive seeds comprising encapsulated radioactive sources (see U.S. Pat. No. 4,815,449; U.S. Pat. No. 4,994,013; U.S. Pat. No. 5,163,896; U.S. Pat. No. 5,575,749; WO 93/04735, which are incorporated by reference) meets the criteria for reducing the potential of isotope leaching during in vivo use, however, these devices result in high levels of micro-localized emissions of radiation at the location of the radioactive seed within the implant. Therefore, a significant drawback with such a device is the non-homogeneous delivery of ionizing radiation. In order to produce devices that exhibit negligible leaching and uniform isotope distribution, methods of ion implantation, wherein the isotope is imbedded within the structure of the stainless steel or metal device have been explored (U.S. Pat. No. 5,059,166; Fischell et al 1996; Violaris et al 1997). In addition, yields are low and difficult to control. Heavier elements are more difficult to ionize, requiring highly specialized, low reliability ion sources. As well, radioactive contamination of the ion source makes maintenance a safety hazard. Typical methods for the preparation of radioactively treated medical devices include bombarding non-radioactive metallic substrate with radioactive ions or transmutating the base material with protons or neutrons creating radioisotopes internally (e.g. U.S. Pat. No. 4,702,228; U.S. Pat. No. 5,405,309). Published work on pilot scale manufacturing methods of stents produced in this manner have been disclosed (Fehsenfeld et al 1991), however, these approaches for the preparation of radioactive devices are limited since they are one-at-a-time processes or involve extensive specialized equipment. Furthermore, only a range of substrates can be used that are compatible with the implantation technologies thereby limiting the selection of materials that can be used for the preparation of radioisotope-treated devices. For example palladium, enriched with palladium-102 can be used for transmutation by exposure to neutron flux, to produce palladium-103 (e.g. U.S. Pat. No. 4,702,228). Transmutation technologies utilizing protons or neutrons would also result in significant undesirable isotopes and associated radiation exposure to the patient in vivo. Furthermore, recovery costs for transmutation methods are high.

A dominant barrier for the application of the use of radioactively treated medical devices has been the lack of a commercially viable method for affixing the radioisotope to a medical device that meets the low leaching criteria required within the art.

Several reports comment, or mention in passing, the option of coating the surface of a medical device such as a stent with a radioisotope of interest (e.g. U.S. Pat. No. 5,213,561; Hehrlein 1995). However, no methods are provided for the preparation of such coated devices, nor are there any methods provided that could be used for the preparation of coated devices that would be suitable for medical application. Rather due to the stringent requirements of negligible, or no, isotope leaching from the radioactive device (e.g. Fischell et al 1996), coated medical devices have received poor reception within the art as it is expected that the coated radioisotope will leach while implanted in vivo. For example, Hehrlein et al (1995) differentiate radioactive stents produced using ion implantation, the use of which they characterize within their study for medical applications, from a coated stent which they considered to be non-applicable and lacking medical utility due to the expected degree of leaching, especially if the medical device needs to flex in any manner. The idea being that a coating would simply flake off the surface of the device and possibly enter the circulatory system.

An alternate solution for treating the exterior of a device has also been proposed that involves electroplating the device, for example with gold-198 (U.S. Pat. No. 5,059,166; U.S. Pat. No. 5,176,617). This latter method applies to a limited range of isotopes and substrates that would be capable of being plated. It is, therefore well recognized within the art that present methods of coating devices with radioisotopes are deficient for the preparation of devices for use in radiotherapy.

There are many benefits associated with radiochemically coating devices. For example, the process is commercially scalable and allows for batch processing of high purity radioisotopes. Such a process combines uniform fixing and apyrogenic attributes for in vivo use, which is particularly important for high volume production. A large range of radioactivity and isotopes can be affixed uniformly, producing homogeneous coatings on a device and allowing customization of product. This process has a high utilization of isotopes, making it clean and efficient compared to other affixing methods. Furthermore, radiochemical coating of devices could utilize isotopes that are otherwise not available in devices prepared by ion implantation or transmutation methods. Similarly, a range of surfaces and non-metallic materials including synthetics, or other bio-compatible materials, could be coated with radioisotopes of interest for use. Thus there is a need to develop a simple method for preparing radioactively treated medical devices so that the radiochemical coating exhibits negligible or no leaching of the isotope in a test solution, or when implanted.

One study has examined the relative absorption of ions in dilute aqueous solutions on glass and plastic surfaces in order to determine the degree of contamination of these surfaces following their exposure to a range of isotopes (Eichholz et al 1965). The method employed adding the desired radioisotope to hard or distilled water and immersing the glass or plastic substrate within this solution for various lengths of time. Following a rinsing step using distilled water, the substrate was dried at 100° C. and the remaining radioactivity of the substrate determined. They note that increasing the concentration of ions in the water-isotope mixture reduced the contamination of isotope on the substrate surface, and that decreasing the pH of this mixture also reduced contamination. No methods are disclosed that attempt to optimize the coating of the substrates with a radioisotope, nor is there any suggestion or disclosure of the use of such a method for the preparation and use of an isotopically coated device. Furthermore, there is no teaching of how permanent the coating of the substrate is, nor is there any information as to the degree of leaching of the isotope from the coated substrate. Rather, Eichholz et al were interested in reducing or eliminating radioactive contamination of glassware, whereas the method of this invention is directed to producing a uniform distribution of radioisotope on the surface of a medical device, as well as maximizing the yield and permanently affixing the radioisotope on the surface of the medical device.

It has been observed that following the method of this invention, coated devices can be produced with high yield, if this is desired, with the coating applied in a uniform manner. Furthermore, leaching of the isotope from the surface of the coated substrate is markedly reduced over other processes for coating a surface of a substrate, for example, that involve a step of heating to dryness in order to affix the radioisotope onto the surface of the device. Lastly, the method of this invention is readily applied to batch processing of a device to be coated, ensuring that coated substrates are produced with consistent coatings both within and between batches.

SUMMARY OF THE INVENTION

The present invention relates to a radioisotope affixing process to chemically cover a substrate in order to render the substrate coated with a radioactive component. This invention is also directed to cardiac and generic stents have been coated with P-32 and Y-90.

According to the present invention there is provided a method for coating a substrate with a radioisotope comprising immersing the substrate within a solution containing a $\gamma$, $\beta^+$, $\alpha$ or $\beta^-$ emitting radioisotope, exposing the substrate to tuned vibrational cavitation to produce a coated substrate, baking the coated substrate at a temperature below the recrystallization temperature of said substrate, rinsing said coated substrate and drying said coated substrate.

This invention also relates to a method as described above wherein the radioisotope is selected from the following groups:

Non-metallic: P-32, P-33, C-14, S-35, Cl-36, I-125, I-131, I-123, I-124,

Metallic: Y-90, Pd-103, Pd-112, Co-55, Co-57, Co-60, Ag-111, Ag-111, Ag-112, Ag-113, Au-199, Cu-64, Re-186, Re-188, Ir-192, Ir-194, Mo-99, Ni-63, In-111, Tc-99m, Rare earths: Ho-166, Gd-159, Pm-142

Actinides: Am-241 preferably wherein the radioisotope is selected from P-32, Y-90, Ag-110, Ag-111, Ag-112 or Ag-113, and more preferably wherein the isotope is P-32 or Y-90.

This invention also encompasses the above method the step of immersing the substrate into a solution containing a $\gamma$, $\beta^+$, $\alpha$ or $\beta^-$ emitting radioisotope, includes an appropriate immersion matrix to enhance coating of the substrate. Furthermore, the baking step of the above method may include temperatures above 100° C. It is also contemplated that the temperatures may range from about 250° to about 420° C.

This invention is also directed to a method as defined above wherein the rate of leaching of the isotope from the coated substrate prepared following the rinsing step is below 0.2% per 15 minutes.

It is also contemplated that the above method may be performed manually or using an automated process. Furthermore, this invention also includes coating of substrates wherein the substrate is a medical device.

This invention also encompasses the above method wherein the step of tuned vibrational cavitation includes an ultrasonic bath. It is further contemplated that an embodiment of this invention may also include the above method wherein the appropriate immersion matrix is an aqueous salt solution.

The method of this invention can be used with a metallic or nonmetallic substrate.

This invention is further directed to a radioactively coated medical device characterized in that the radioactive coating exhibits a rate of leaching of the isotope from the substrate of below about 0.05% per 15 min. More preferably, the rate of leaching is below about 0.007% per 15 min.

It is also contemplated that this invention is directed to a method of treating a patient in need thereof, comprising administering the coated radioactive device as defined above. Furthermore, this invention is directed to the use of the coated radioactive device as defined above for the treatment of cell proliferation.

Substrates coated using the method of this invention, are produced with a uniform coating, improving over methods that simply employ evaporating the radioisotope to dryness. Furthermore, these coated devices can be produced with a high yield of radioisotope, and exhibit negligible, industrially or medically acceptable, rates of leaching of coated isotope. Lastly, the method of this invention is readily used for batch processing devices, thereby ensuring that coated substrates are produced with consistent coatings both within and between batches.

BRIEF DESCRIPTION OF THE DRAWINGS

These and other features of the invention will become more apparent from the following description in which reference is made to the appended drawings wherein:

FIG. 10A shows a uniformly coated stent;

FIG. 10B shows an unevenly coated stent with a greater loading of isotope on one end of the stent from the other;

FIG. 10C shows another coated stent revealing a saddle shaped loading of radioisotope.

DESCRIPTION OF PREFERRED EMBODIMENT

Figure 1:
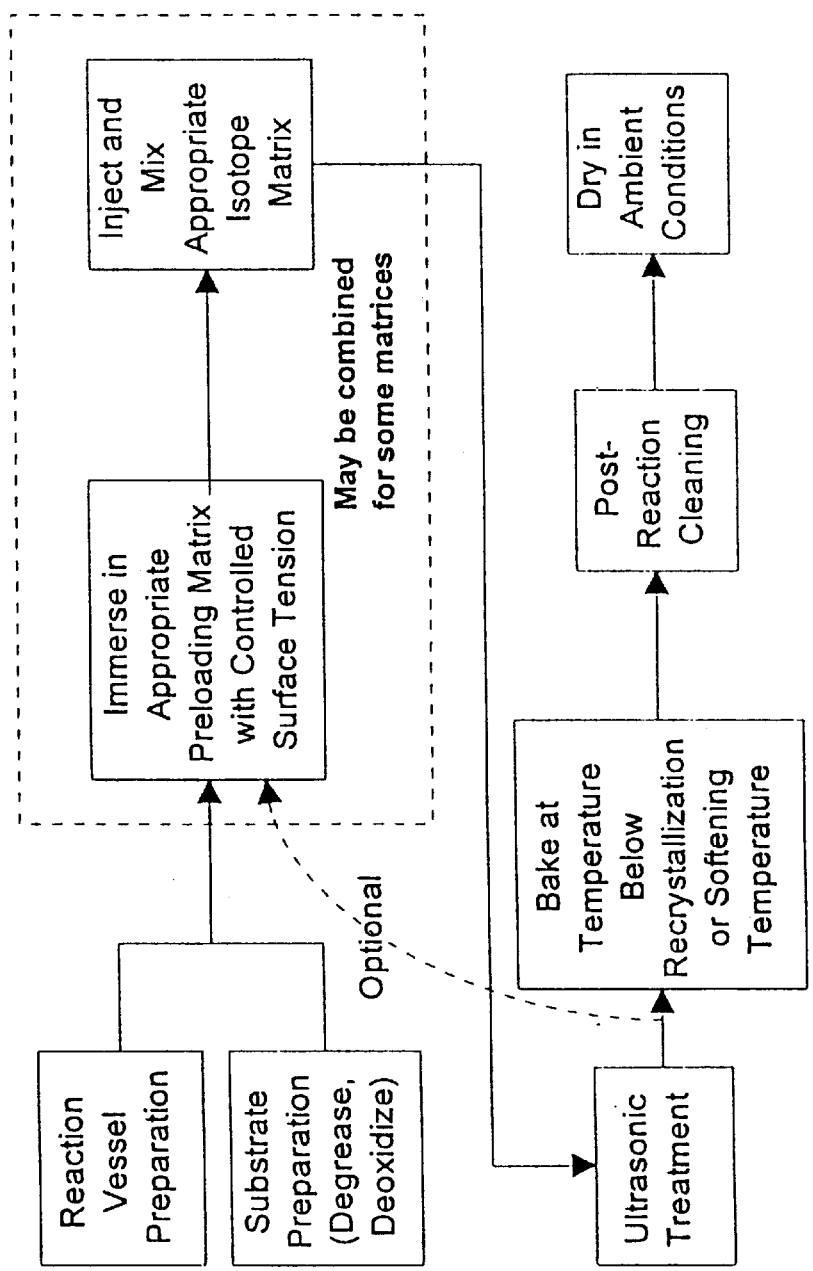
FIG. 1 outlines one of several possible methods of affixing radioisotopes onto medical devices.

This invention is directed to producing a radioactive coating on medical devices. More specifically, this invention embraces the coating of implantable medical devices such as stents, catheters, radioactive seeds and the like for use in medical treatments with at least one radioisotope of interest.

The method of this invention provides for a number of medical devices, implants, and sources to be made radioactive using a radioisotope of interest, typically selected from $\gamma$, $\beta^+$, $\alpha$, or $\beta^-$ emitting radioisotopes, or a combination thereof. The radioisotopes of the following list, while not to be considered as limiting, may be used in accordance with the method of this invention:

Non-metallic: P-32, P-33, C-14, S-35, Cl-36, I-125, I-131, I-123, I-124,
Metallic: Y-90, Pd-103, Pd-112, Co-55, Co-57, Co-60, Ag-110, Ag-111, Ag-112, Ag-113, Au-199, Cu-64, Re-186, Re-188, Ir-192, Ir-194, Mo-99, Ni-63, In-111, Tc-99m,
Rare earths: Ho-166, Gd-159, Pm-142
Actinides: Am-241
preferably wherein the radioisotope is selected from P-32, Y-90, Ag-110, Ag-111, Ag-112 or Ag-113, and more preferably wherein the isotope is P-32 or Y-90.

It is also contemplated that mixtures of any of the above isotopes may also be used with the method of this invention so that medical devices coated with several isotopes capable of emitting a range of radiation doses (i.e. varying strengths of ionizing radiation), or for varying lengths of time may be produced.

By "medical device" it is meant any apparatus that is used for the treatment of a medical ailment, and that can be treated in such a manner as to deliver ionizing radiation at a site requiring such treatment. The substrate of the medical device may be metallic or non-metallic in nature, as long as there is some affinity of the substrate for the radioactive chemical that is used for the coating process. Metallic substrates include, but are not limited to, zinc, titanium, platinum, tantalum, palladium, stainless steel, zirconium. Non-metallic substrates include, but are not limited to plastics such as nylon, Teflon® and the like, or other suitable polymeric materials, as well as glass. Furthermore, expandable devices have been successfully loaded with radioisotopes using the method of this invention with the same rates of leaching after changing the shape of the device, as non-expandable devices.

Typically the medical device is implanted, however, it may also be reversibly inserted within, and traverse the length of, an already implanted device such as a catheter (e.g. WO 93/04735, which is incorporated by reference). Furthermore, these devices may be applied on the exterior of a site requiring treatment should such a need arise. While not intended to be limiting in any manner, medical devices that may be coated using the method of this invention may include stents, expandable stents, catheters, seeds, protheses, valves, staples or other wound closure devices as would be recognized by one of skill in the art. These devices may be of arbitrary shape and for any purpose, that requires the use of a radioactively treated medical device. Furthermore, it is contemplated that "medical device" also includes substrates that can be coated with a radioisotope of interest or combination thereof, and used as a radioactive source within encapsulated structures such as seeds (e.g. U.S. Pat. No. 5,163,896; U.S. Pat. No. 4,994,013; U.S. Pat. No. 4,815,449; U.S. Pat. No. 5,405,309; U.S. Pat. No. 4,702,228, which are incorporated by reference), delivery wires (e.g. U.S. Pat. No. 5,575,749) or the like as would be well known to one skilled within the art. These encapsulated structures are also considered to be medical devices.

By "immersion matrix" it is meant the solution that the medical device is placed within before, or during, the coating procedure. The immersion matrix may comprise a range of ingredients directed at increasing the affinity of the surface of the medical device to receive a radioisotope of interest, or the immersion matrix may also be selected to enhance the coating of the medical device with the selected radioisotope of interest, or both. The immersion matrix may also be selected to help drive the radioisotope from the solution and onto the surface of the medical device.

Without wishing to limit the compositions that the immersion matrix may comprise in any manner, it is contemplated that the immersion matrix may consist of water, or water containing a salt or combination of salts, and optionally a buffer, or the immersion matrix may comprise other reagents such as an alcohol. However, the immersion matrix may comprise other ingredients as deemed necessary. The composition of the immersion matrix can comprise any ingredient which is capable of being safely used for tuned vibrational cavitation providing it does not chemically react in an aggressive fashion with either the substrate or radiochemical. It has been noted that in some instances the addition of salt is more effective in enhancing the yield of coated isotope than water alone, however, the selection of other compositions may also prove effective for increasing overall yield. If a salt is selected as a component of the immersion matrix, a range of concentrations may be used in order to enhance the coating of the medical device. Without wishing to be limiting in any manner, a range of salt concentrations from about 0.05 to 20% (w/v) is contemplated, or more preferably with a range from about 0.1 to 5% (w/v). It has also been observed that the use of ultra pure chemicals aids in the coating process.

Figure 2:
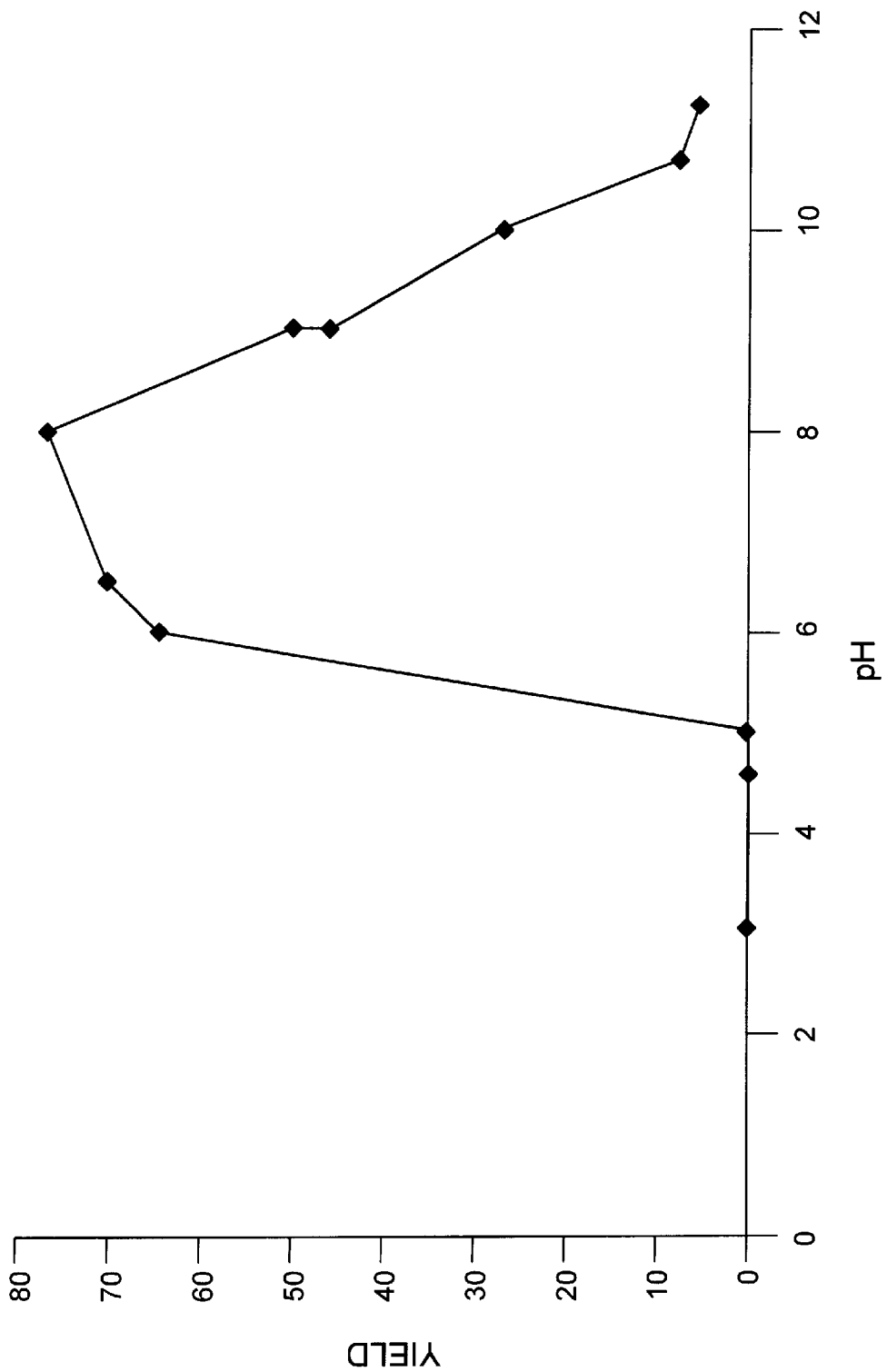
FIG. 2 shows the effect of pH on the yield of a stainless steel stent coated with Y-90.

It is also contemplated that the pH of the immersion matrix is selected to increase the efficiency of the coating process. A range of pH may be used, however an embodiment of this method utilizes a range from about pH 4.0 to 11 and will depend upon the radioisotope used. For example, for Y-90 an effective range of pH is between from about pH 5.5 to 10.5 (see FIG. 2).

The immersion matrix may also comprise agents to alter the surface tension of the solution. For example, without wishing to limit the selection of such agents in any manner, an agent may include ionic or non-ionic detergents, or alcohol.

Figure 3:
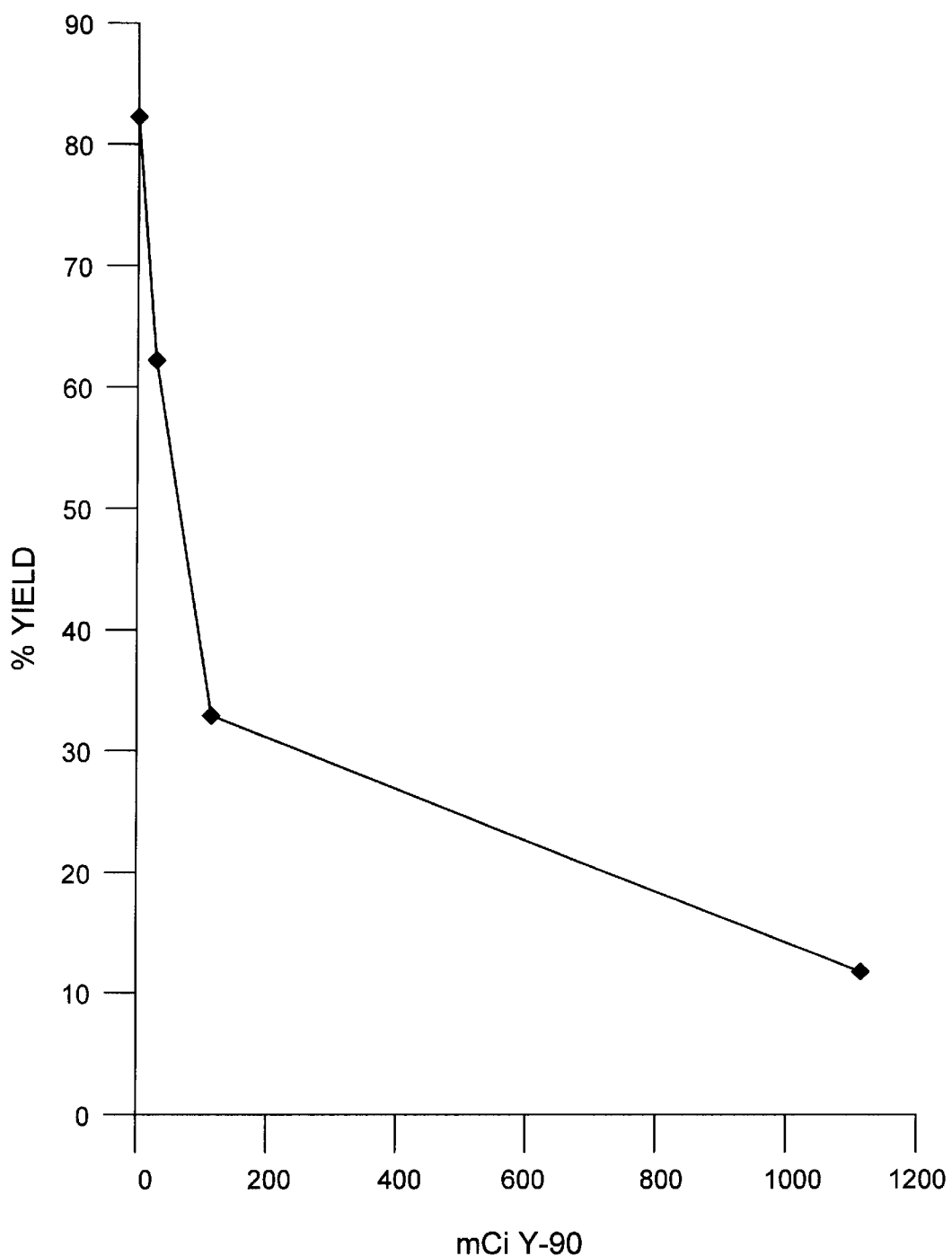
FIG. 3 shows the percent of radioactivity (of the total isotope added to the immersion matrix) adsorbed onto the surface of a stainless steel stent over a range of concentrations of radioisotope present within the immersion matrix. With increasing radioisotope concentration, the percent of radioactivity (i.e. % yield) decreases, however, the amount of radioisotope coating the substrate (not shown in this figure) increases. The isotope used in this analysis is Y-90.

By "yield" it is meant the amount of radioisotope remaining on the surface of the medical device or substrate as prepared using the method of this invention. The yield is determined from the amount of radioisotope added to the immersion matrix. Following the method described below, yields of about 80% have been routinely obtained. This value is to be compared with the method of Eichholz et al, which produce coated substrates with yields of about 5% (see below). Typically a higher amount of radioisotope coating can be obtained by adding more radioisotope to the immersion matrix, however, the yield decreases with increased concentration of isotope within the immersion matrix (FIG. 3). Even though yields of 80% can be routinely obtained, more uniform coatings of the substrate are observed with yields of about 40–60%.

It has been observed that very low rates of leaching are detected, following the method of this Invention, irrespective of the yield. That is to say, that acceptable rates of leaching of an isotope from a coated substrate are obtained using the method of this invention whether the yield is from about 40–60%, or 80%.

Typically, the medical device is immersed within the immersion matrix prior to the addition of the radioisotope of interest. The isotope is then added to the immersion matrix, without exchange of the immersion matrix. However, it is contemplated that more than one immersion matrix may be used for the coating process and that the medical device could be placed within one or more immersion matrix solutions prior to exposure to an immersion matrix comprising a radioisotope of interest.

By "tuned vibrational cavitation" it is meant any method of activating the immersion matrix so as to form bubbles of various sizes and states within the immersion matrix that are capable of collapsing thereby imparting shockwaves within the immersion matrix to help drive the isotope onto the surface of the medical device. Tuned vibrational cavitation may impart a range of shockwave forms to the immersion matrix. It has been observed that square or sinusoidal wave forms can be effectively used in the method of this invention. However, tuned vibrational cavitation comprising wave functions of a variety of forms, frequencies, amplitudes, or complexities, or mixtures of frequencies, amplitudes or wave forms, that aid in driving the isotope of interest onto the surface of the medical device, can be used with the method of this invention. Examples of eliciting tuned vibrational cavitation include, but are not limited to, laser tuning (which can be used vibrate and excite molecules e.g. Wizemann et al 1997; Arlinghaus et al 1997) microwave or ultrasonic treatments of the immersion matrix. However, other means of imparting shockwaves within the immersion matrix may also be used, for example high temperature, modified pressure etc. If ultrasonic treatment is employed as a source of tuned vibrational cavitation, then a square wave function may be selected for the coating step, as such wave forms have been observed to enhance the coating of the medical device. Without wishing to be bound by any theory, shockwaves produced using a square wave function, impart to the immersion matrix, and the radioisotope of interest, a higher energy when compared with shockwaves produced by sinusoidal waves. Sinusoidal waves may be useful in the rinse stages of the coating method of this invention. However, there may be applications where sinusoidal wave functions may be employed to coat the medical device. As an example, an immersion matrix that comprises a mild buffering solution maintaining pH at about 8, and 1% saline, an ultrasonic treatment of 10 min has proved sufficient for producing a high yield coating (>80%) on stainless steel stents with Y-90.

Figure 4:
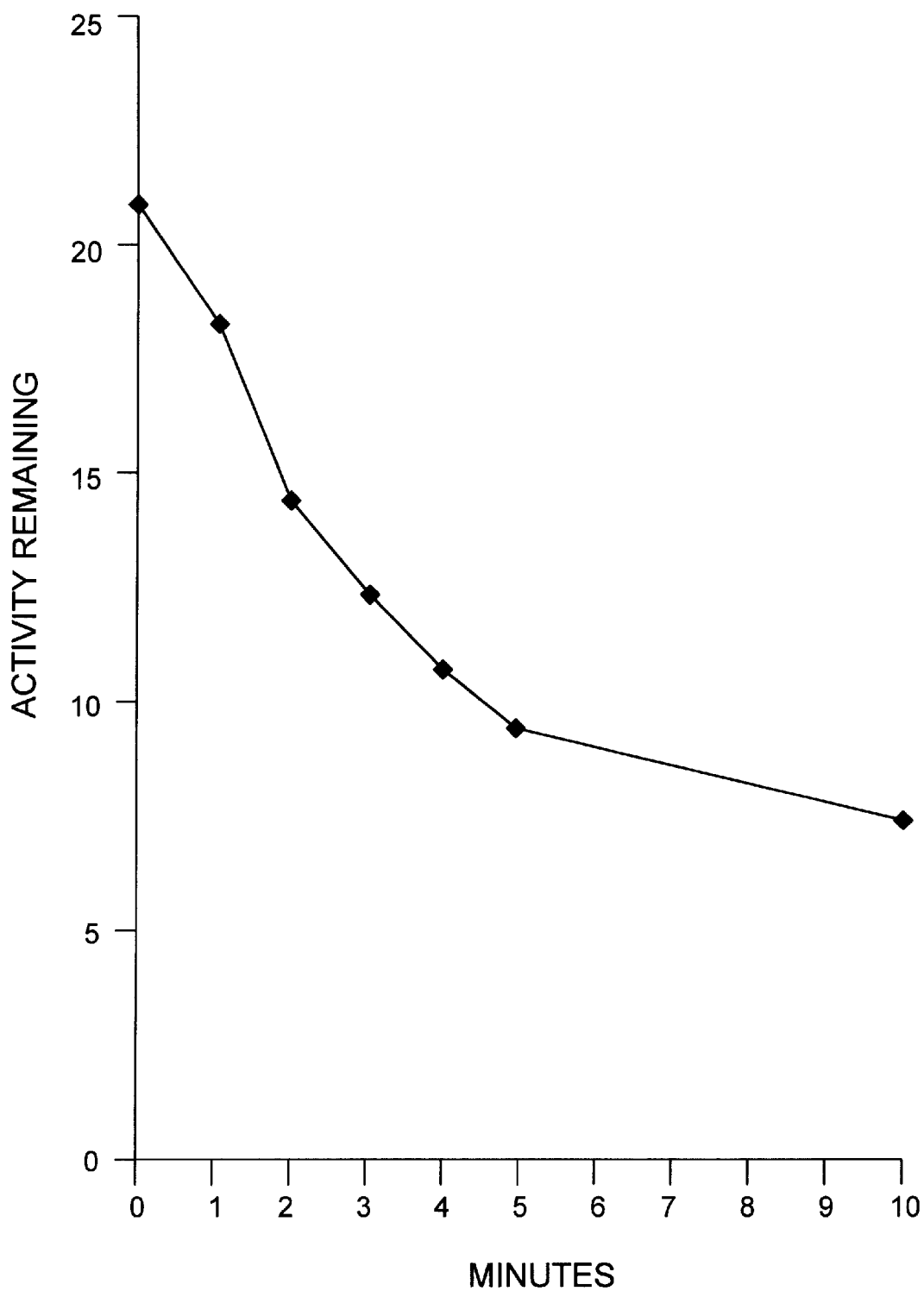
FIG. 4 shows the rate of removal of radioisotope from the immersion matrix as it is deposited onto the surface of the substrate being coated during the step of tuned vibrational cavitation. The data is for a 15 mm stainless steel stent immersed in 1% NaCl, 0.1% $NaHCO_3$ ultrasonic treatment, coated with Y-90.

Typically the substrate to be coated is exposed to tuned vibrational cavitation, in the presence of radioisotope, from about 5 min to 3 hours, depending upon the coating desired on the substrate. It has been found that varying the time of the ultrasonic step is one variable that effects the yield of the coated substrate. However, this time variable may have less impact on yield if the appropriate immersion matrix is selected, since high yields have been observed with short (5–10 min) exposures to tuned vibrational cavitation. The rate of the coating procedure can be monitored during the step of tuned vibrational cavitation. For example, FIG. 4 shows the rate of removal of a radioactive isotope from the immersion matrix during ultrasonic treatment as it is deposited onto the surface of the immersed device.

There is a relationship between the rate of deposition of a substrate being coated using tuned vibrational cavitation, and the uniformity of coating along the length of the stent. For example, it has been observed that both longitudinal and radial uniformity (defined below) increases with slower deposition rate. However, by using higher rate of deposition, saddle-shaped stent coatings can be obtained (e.g. see FIG. 10C). It is contemplated that a stent coated in this manner may have applications if it is desired that the ends of the stent incorporate higher radioisotope loadings. The rate of deposition is affected by the pH and temperature of the solution, as well as by the surface area (of the substrate) to volume (of the solution) ratio, and the intensity of the ultrasonic treatment. Without wishing to limit the method of this invention in any manner, we have found that uniform coatings on stents, with yields in the order of 40%, can be obtained by using a 15 mm stent:2 ml vol of immersion matrix ratio, at pH 6, and incubating at 50° C. with 10 min of ultrasonic treatment.

Figure 6A:
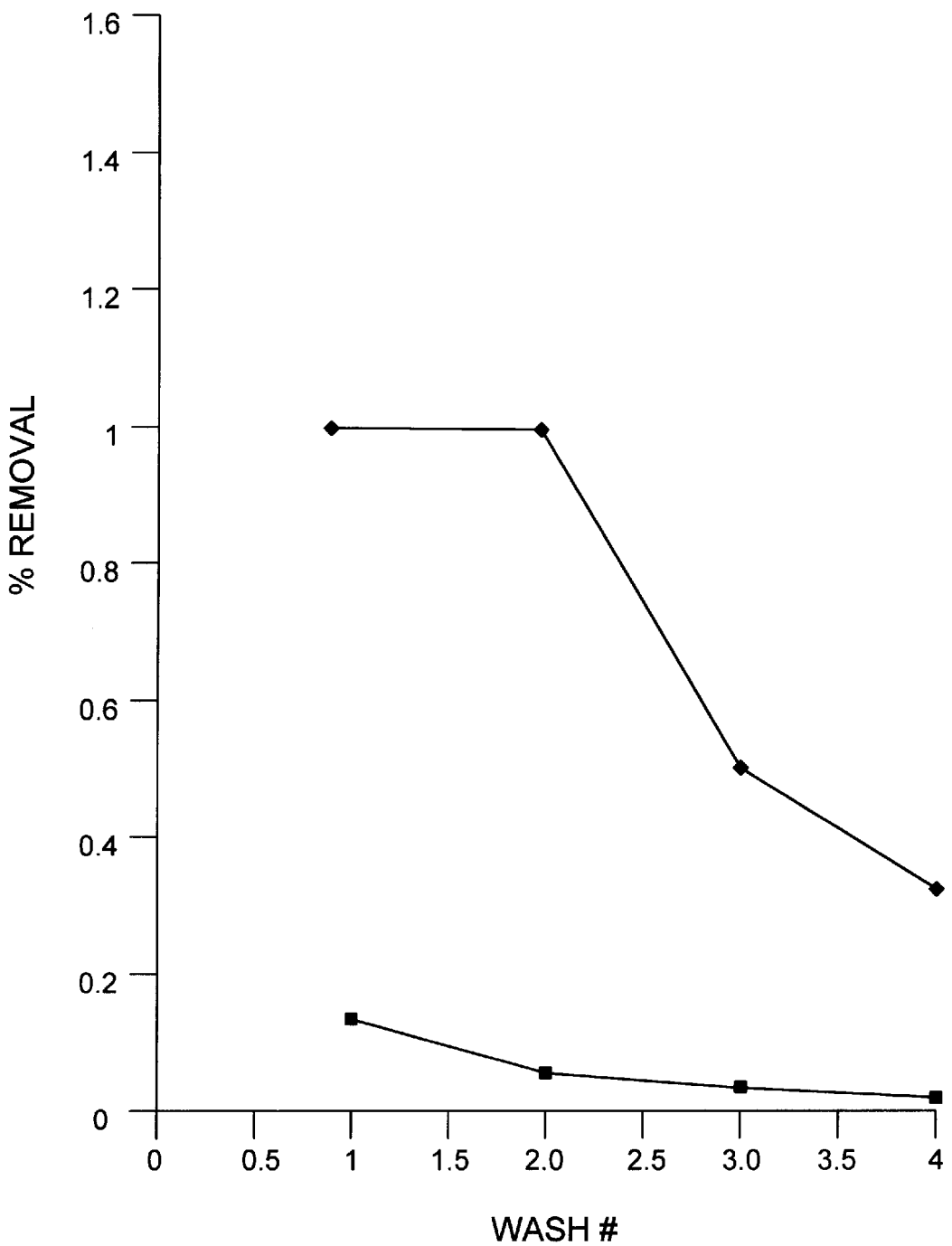
FIG. 6 shows a comparison between the rate of leaching of radioisotope from surfaces coated using either the method of this invention involving the step of tuned vibrational cavitation (♦), or a step involving heat-evaporation (■) for either Y-90 (FIG. 6A), or P-32 (FIG. 6B).

Following the method of this invention a distinct improvement is observed in the rate of leaching of a radioisotope from the surface of a coated substrate when compared with other coating techniques (such as those derived, for example, from Eichholz et al, 1965). For example, if the step of "loading" the isotope onto the surface of the substrate, using tuned vibrational cavitation is replaced with a step involving heating the substrate (after exposure to the immersion matrix for equivalent lengths of time) at 200° C. to dryness, a marked increase in the leaching rate is noted (see FIGS. 6A, for Y-90, and 6B, for P-32).

Figure 5:
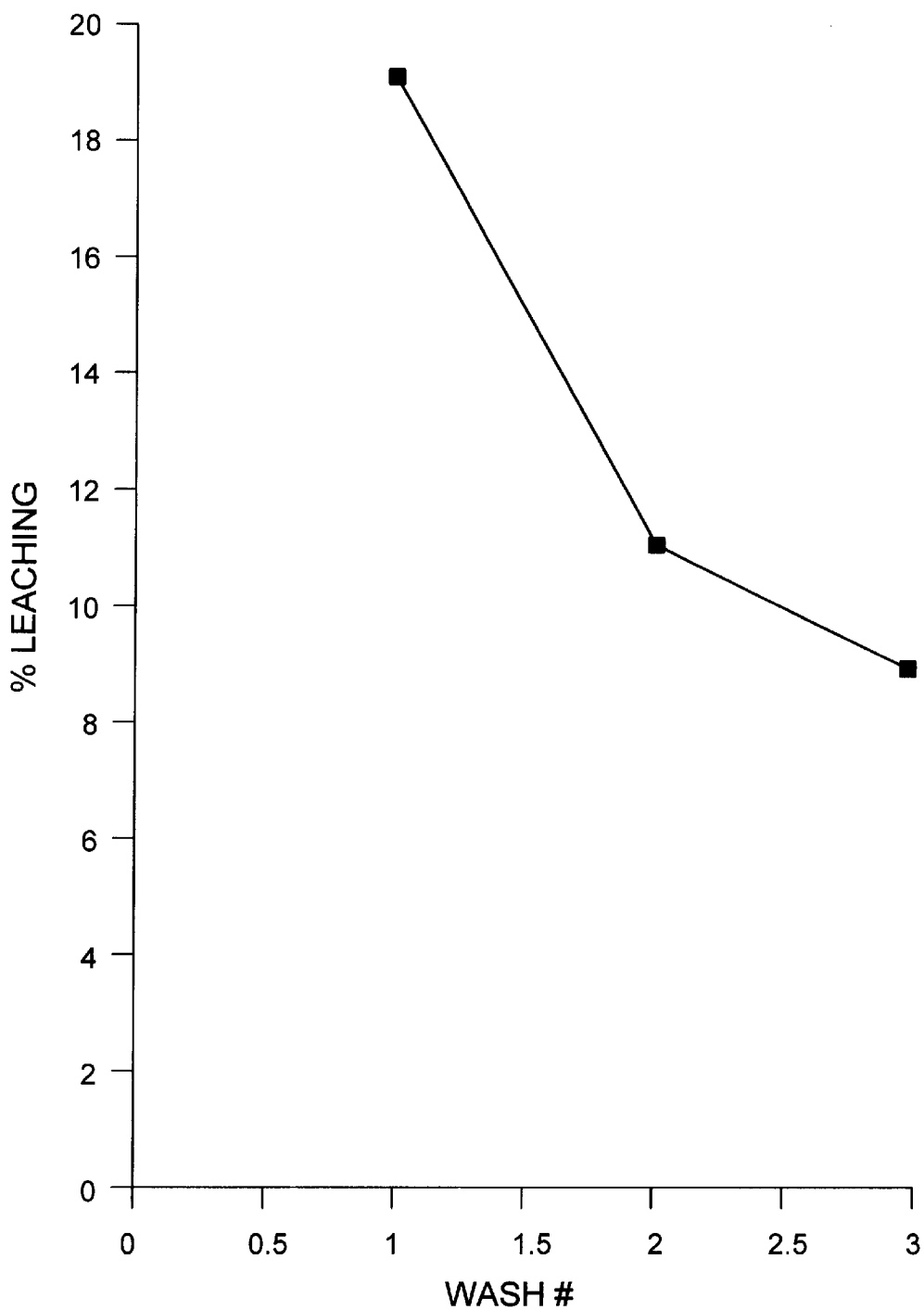
FIG. 5 shows a comparison in the rate of leaching between a stent baked for 30 min at 300° C. (♦), and a non-baked stent (■), when coated with Y-90.

By "temperature below the recrystallization, or softening temperature of the material comprising the medical device" it is meant a temperature that does not alter the physical properties of the medical device so as to affect the function or other desired characteristic of the medical device. Any selected temperature must also not adversely effect the properties of the selected radioisotope. This temperature may reach 1,500° C. or more depending upon the substrate being coated. For example, radioactively coated glass has been baked above the melting temperature of glass without adverse effects on the substrate-isotope coating. Typically the maximum baking temperature will be determined by the substrate of the medical device, rather than the radioisotope used for coating. Temperatures contemplated for baking the coated medical device include from about 150° to about 1,500° C., and typically range from about 200° to about 600° C., more preferably from about 250° to about 450° C. A comparison of the rate of leaching of stents coated using the method of this invention, but differing with respect to the use of the baking step can be seen in FIG. 5. Without wishing to be bound by theory, this step aids in the curing of the coated radioisotope with the surface of the substrate of the medical device and helps ensure the formation of bonds between the isotope and surface of the medical device.

By "coated medical device" it is meant a medical device that is coated using the method of this invention. If the coated medical device is to be used directly for in vivo applications, then the rate of leaching of the radioisotope from the surface of the medical device, as determined by sampling of the rinsing solution after 15 minute ultrasonic leaching in normal saline at 37° C., should be less than 0.1% of the total amount applied, is preferably less than about 0.05%, and more preferably less than 0.01% per 15 minutes. Coated medical devices, such as stainless steel stents, have repeatedly been produced by the current process with removable contamination levels on the final leaching test of less than 0.01% using Y-90 (see FIG. 6A). However, it is also contemplated that coated medical devices may also be encapsulated in some manner as is known within the art, in the form of a seed. In this application, the coated device may not require the same stringent degree of leaching as desired for coated medical devices that are used for direct implantation applications. Rates of leaching that are considered suitable for the coating of a device range from about 0.1% to 0.001%.

By "uniformity" of the coated surface it is meant the consistency of radioactive emission detectable along the length (longitudinal uniformity), and optionally, depending upon the shape of the substrate being coated, uniformity may also be determined in a second dimension. For example with stents, routine uniformity analysis involves assessment of the longitudinal uniformity (see FIGS. 9 and 10), as well as radial uniformity (see FIG. 8).

The level of radioactivity of the coated medical device can be tailored to achieve a range of therapeutic doses by varying the amount supplied to the immersion matrix.

With reference to FIG. 1, there is outlined one aspect of an embodiment of the method of this invention. Typically the method involves:

1) preparing the reaction vessel used for coating the medical device, as well as the medical device itself prior to initiating the coating procedure. The purpose of this step is to expose the maximum amount of the surface of the substrate to the coating process by removing any impurities. Any method of treatment of the reaction vessel or medical device may be included within this step ensuring compatibility between the substrate and cleaning material. This treatment may include degreasing and/or deoxidizing the surface of the vessel, and medical device as indicated within FIG. 1. Suitable compositions for such treatment include, but are not limited to nitric, citric, or chromic acids. Ideally, the selected cleaning material is to be adopted to the substrate being coated, and such selections are know to those skilled in the art;

2) immersing the medical device in the appropriate immersion matrix;

3) adding the isotope of interest to the immersion matrix;

4) exposing the immersed medical device to tuned vibrational cavitation for a period of time to sufficiently drive the isotope of interest onto the surface of the medical device. This step may take place at a temperature that significantly deviates from ambient temperature in order to optimize coating of the medical device;

5) optionally re-immersing the medical device in a new immersion matrix. The new immersion may comprise more of the same radioactive isotope as in the initial immersion matrix, or may comprise a new immersion matrix composition comprising an alternate radioisotope and repeating the exposure to tuned vibrational cavitation;

6) rinsing the coated device in water and baking at a temperature below the recrystallization, or softening temperature of the material comprising the medical device;

7) rinsing the medical device to remove radioisotope not permanently affixed to the surface of the medical device. The rinsing solution may be the same or different as the immersion matrix. This step optionally includes the use of tuned vibrational cavitation and may be repeated as needed in order to produce a coated medical device with minimal or no leaching of the radioisotope; and 8) drying the device.

It is to be recognized that the use of specific chemicals within the immersion matrix or rinsing solutions, temperatures of exposing the medical device during tuned vibrational cavitation, baking or rinsing, and the duration of each of these steps, can be modified and will be a function of the radioisotope, the substrate material of the medical device as well as the geometry of the medical device that is being coated. The above process is to be considered a guide to the conditions used to obtain a coated medical device.

There are major differences between the method outlined above to those disclosed by Eichholz et al (1965). The affixing process of this invention produces substantially different results from the process described in Eichholz et al. This difference is highlighted by the fact that coated substrates prepared using the method of Eichholz et al result in coating efficiencies of 5% of the initially added radioisotope to the immersion matrix. However, coating efficiencies obtained using the method of this invention produce coated substrates yielding greater than 70% efficiencies, and routinely substrates are prepared comprising about 80% of the radioisotope added to the immersion matrix. Furthermore, substantial rates of leaching (e.g. above 0.2%) of the coated substrate produced by the method of Eichholz et al are observed after 3 or more rinsing steps, however, as indicated above, rates of leaching of less than 0.05% are produced by the method of this invention.

The differences between the method of this invention and that of Eichholz et al that produce coated substrates with such differing properties include:

a) Choosing the appropriate immersion matrix is important in obtaining a coated substrate with uniform distribution and high yield of isotope. Using the process described herein, radioactive P-32 and Y-90 substrate coatings on stents have routinely achieved longitudinal uniformities of at least ±15%, and radial uniformities of at least ±10%. Eichholz et al disclose that the use of hard water or salt dramatically reduces radioactive contamination of glassware. For example, Eichholtz et al report that the addition of 0.2% (w/v; equivalent to 0.02N) $CaCl_2$ was effective in abolishing the adsorption of Cs-137 on glass (e.g. see FIG. 2 of Eichholz et al). However, using the method of this invention, the addition of salt (from about 0.05 to 20% (w/v), or from about 0.1 to 5% (w/v), or more preferably from about 0.5 to 3% (w/v)) and buffer (an amount sufficient to maintain the desired pH) has been found to dramatically increase the yield of the coating of radioisotopes of interest. Using 1% saline as the immersion matrix, at a pH of 7–10, yields of coated substrates in the order of 70% are routinely obtained. Furthermore, the addition of a buffer to the saline immersion matrix increased yields of about 90%. Therefore, according to the method of this invention, selection of appropriate salt and buffer compositions will be important in achieving high coating efficiencies. However, it is to be noted that even in the absence of any added salt or buffer within the immersion matrix, yields of about 35% are obtained using the method of this invention and water (depending upon the pH of the water).

b) The use of tuned vibrational cavitation has been observed to dramatically increase the yield of isotope on the surface of a substrate prepared using the method of this invention. It has been observed that while the method of Eichholz et al results in yields on a rinsed coated surface (such as stainless steel) of 5%, when the same substrate is prepared with water as the immersion matrix, by adding the step of tuned vibrational cavitation and other steps of this method being kept constant, yields of at least 35% are routinely observed. Without wishing to be bound by theory, it is thought that the step of tuned vibrational cavitation enhances nucleation, that is, this step is thought to enhance precipitation of the radioisotope onto the surface of the substrate.

c) The baking step also increases the adherence of the radioisotope to the substrate. In comparison, the 100° C. baking step of Eichholz et al is used to increase the rate of drying of the glassware under test and no parameters are disclosed to produce or test permanently affixed coatings. Without a baking step, leaching of the coating is enhanced in a saline rinse solution. For the process described herein, yields greater than 35% have been routinely achieved using water as the immersion matrix, after rinsing radioactively coated substrates in an ultrasonic bath following a baking step. Without wishing to be bound by theory, it is proposed that high baking temperatures provide energy to allow the radioactive molecules to enter the substrate molecular structure to form chemical bonds as well as promoting oxide layer formation. Both of these properties (forming bonds with the substrate and promoting oxide layer) enhance the yield and coating efficiencies of the method of this invention by ensuring that the coated radioisotope remains affixed to the substrate. In general it has been observed that while tuned vibrational cavitation increases the amount of radioisotope that is able to coat and penetrate the substrate, baking ensures that the isotope coating bonds to the substrate.

It is contemplated that the steps of the method of this invention can be performed either manually or automated, and cover a range of radioactivity.

The following examples, while exemplifying the method and preparation of coated medical devices, are not to be considered limiting as to the scope of substrate, shape, or utility of devices that could be coated.

EXAMPLE 1

Coating of Substrates Using Different Immersion Solutions

Different substrates were exposed to different immersion solutions containing Y-90. The solutions were heated from 50° C., and ultrasonically treated for 1–3 hours. The amount of isotope remaining on the surface of the stents was calculated from the total amount applied to the immersion matrix. The results are presented in Table 1:

TABLE 1

Coating of different substrates with Y-90 using different immersion solutions.

| Substrate & Matrix | Yield |
|---|---|
| SS*: 1N $NH_4OH$ | 50% |
| SS: 1N $NH_4OH$ + 10% EtOH | 60% |
| SS: 5% $NH_4NO_3$ (w/v) | 0% |
| SS: $H_2O$, pH 6.0 | 40% |
| SS: 0.9–3% NaCl (w/v) | 60% |
| SS: 1% NaCl (w/v) ($NH_4OH$ to adjust pH) pH 8–9 | 50 % |
| Tantalum: 1% NaCl (w/v) | 81% |
| Zirconium: 1% NaCl (w/v) | 82% |
| Plantinum: 1% NaCl (w/v) | 68% |
| TEFLON ® (PTFE) 1% NaCl + 0.1% $NaHCO_3$ (w/v) | 30% |
| Glass: 1% NaCl + 0.1% $NaHCO_3$ (w/v) | 45% |

*SS: stainiess steel

The data of Table 1 indicates that Y-90 is capable of being applied to a variety of substrates, including stainless steel, tantalum, zirconium, platinum, TEFLON® and glass in the presence of saline. However, modification of the immersion matrix may have dramatic effects on the interaction between the isotope and substrate (e.g. compare $NH_4OH$ v. $NH_4NO_3$).

Furthermore, it has been observed that equivalent yields are obtained using a variety of surface geometries including, pin and button shaped substrates, or spherical or flat surfaced substrates.

EXAMPLE 2

Optimizing Coating of Substrate with Radioisotopes

Cleaning of Stent:
Stainless steel stents were prepared by using a citric acid and sodium citrate or $HNO_3$ cleaning solutions.
Immersion Matrix:
The cleaned stents were placed into an immersion matrix within a vial so as to totally immerse the stents, followed by addition of radioisotope. The immersion matrix was either ammonia (from about 0.001 to 1N $NH_4OH$), NaCl with sodium bicarbonate, sodium carbonate, or saline (pH 8), for Y-90, sodium nitrate, or ammonium nitrate (pH 6–8) with P-32, respectively, and ethanol (10%) or saline (1%), with the radioisotope being in acid form (either HCl for Y-90 or $H_3 PO_4$ for P-32).
Ultrasonic Treatment:
The loaded vials were placed within an ultrasonic tank at from about 40–80° C, and exposed to tuned vibrational cavitation from 5 min, up to 3 hours. As a comparison, stents were also exposed to heat-induced evaporation in place of ultrasonic treatment. For this treatment, stents were placed on top of a hot plate (approximately 200° C.) for a period of time until dry.

Baking:

The immersion matrix was decanted, and optionally the stents rinsed, dried, placed into a new vial and baked. Baking temperatures ranged from 300 to 420° C., and baking times ranged from about 30 min to 1 hour. The vial containing the stent was removed and allowed to cool.

Washing:

Saline (1%) was added to the vial, and the vial placed in an ultrasonic tank for 15 min, at 50° C. Typically the protocol involves one wash step followed by 3 leaching steps as outlined below.

Leaching:

Saline was added to the vial and the vial placed within an ultrasonic tank. Ultrasonic treatments lasted for 15 min at 37° C. This treatment was typically repeated three times. Aliquots of leaching solution were assayed for radioisotope contamination causing a liquid scintillation measurement device (see FIG. 5, and 6A, B).

Figure 7:
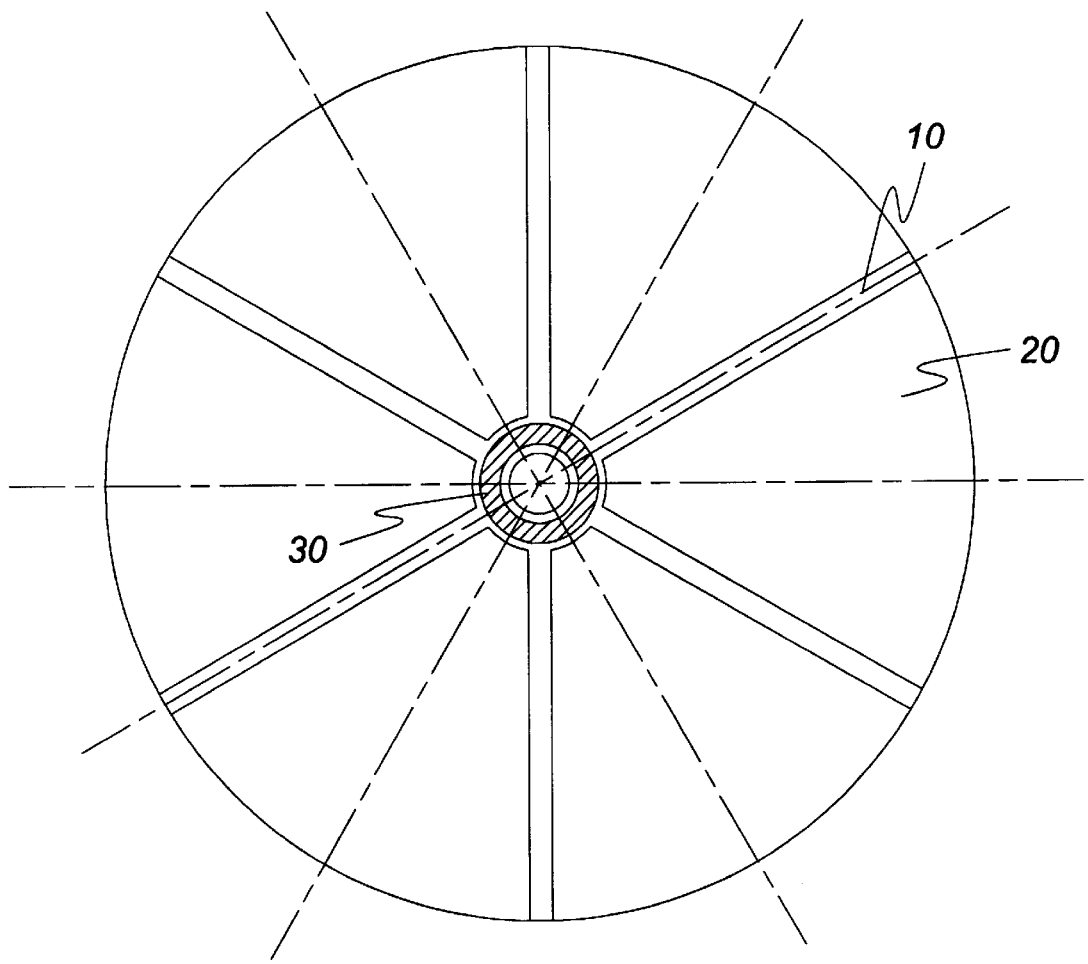
FIG. 7 represents in diagrammatic form the instrument used to test stents for their radial uniformity.
Figure 8:
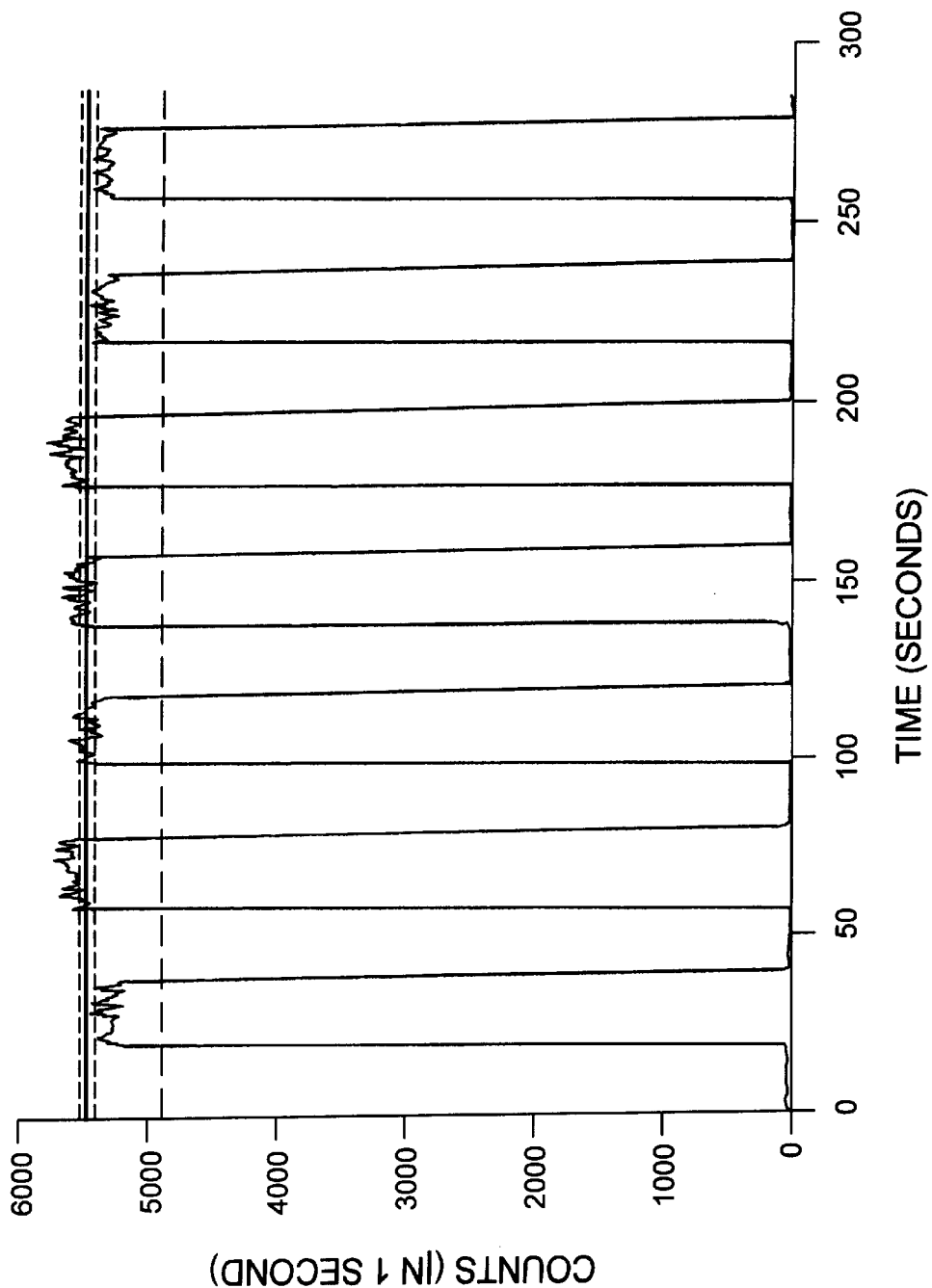
FIG. 8 shows data of uniformity scan analysing the radial uniformity of radioactive emission of a coated stent. The 7 peaks on this graph represent the detection of radioactive emission from the stent as detected using the instrument of FIG. 6.
Figure 9:
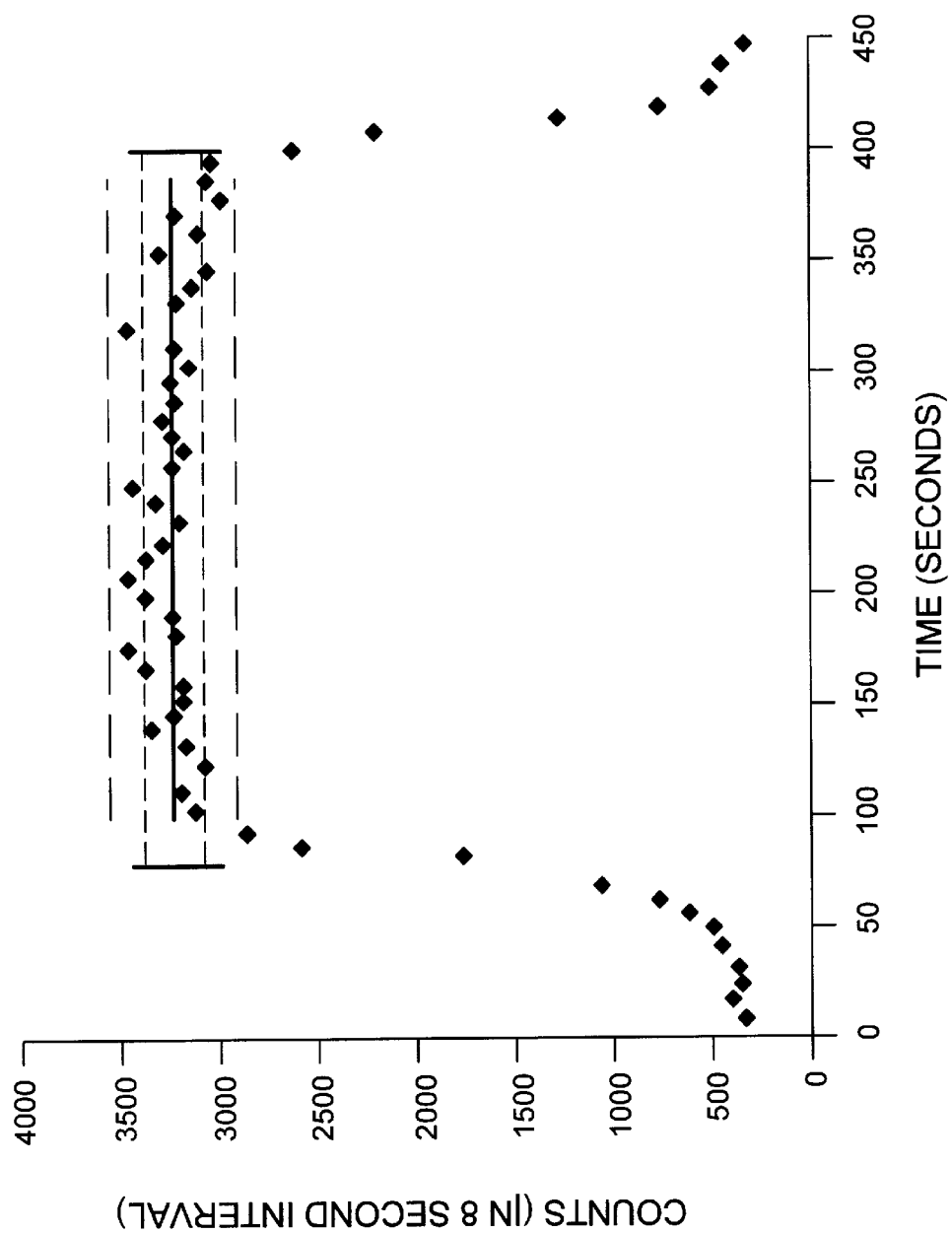
FIG. 9 shows data of a uniformity scan analysing the longitudinal uniformity of radioactive emission of a coated stent. The profile represents the detection of radioactive emission from a stent as the detector is passed along the length of the stent. The two vertical solid bars indicate the length of the stent, the horizontal solid line represents the average detected emission, the horizontal dashed and dotted lines represent deviation (total, or 3 standard deviations, respectively) from the average detected emission.
Figure 10:
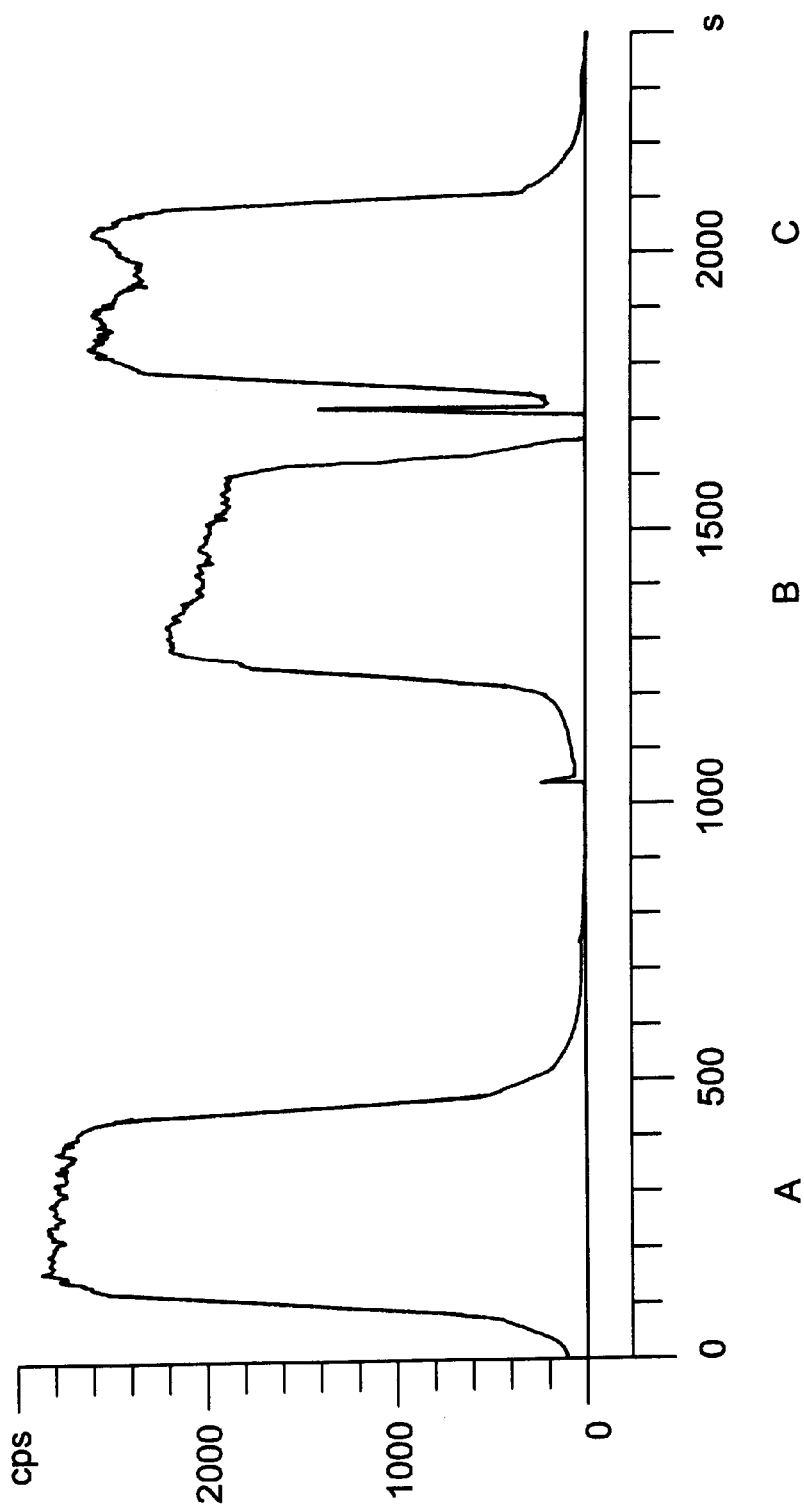
FIG. 10 shows three separate longitudinal uniformity scans for three coated stents.

Uniformity:

Uniformity of the radio coating of the substrate can be detected using any suitable detector. For the purposes of the following examples, a Bioscan Flow-Count radiochromatography detection system which was modified so that accurate radial and longitudinal scans of radioactively coated stents can be obtained, was used. The detector essentially comprises a variety of scintillation crystals. For radial uniformity, the detector is mounted on the outside of a shielding device (20) containing radially spaced apart slits (10; see FIG. 7) and the stent is placed centrally (30) within this device. As the shielded device revolves, any radioactive emissions that escape from the shielded device, through the slits, are registered by the fixed position detector (FIG. 8). Similarly, longitudinal uniformity is analysed by placing the coated stent within a shielded device that contains a longitudinal slit so that the radioactive emissions along the length of the stent can be determined (FIG. 9). Stents coated by the method of this invention, including tuned vibrational cavitation, wherein the yield of radioisotope is about 40–60%, the coating is uniform, both longitudinally and radially (FIGS. 8, 9 and 10A). With higher concentration of radioisotope added to the immersion matrix, and/or with shorter exposure to tuned vibrational cavitation, deviation from uniformity is observed (See FIGS. 10 B and C). Even though these variations in coating uniformity are observed, different applications of stents bearing such modified coatings may be useful if higher emissions are desired at both or one end of the stent.

A) Y-90

Effect of Ultrasonic, Heating to Dryness or Reflux Treatment

Stainless steel stents were exposed for 1 hour in 1N $NH_4OH$/10% EtOH containing carrier-free Y-90 to ultrasonic or reflux treatments, or neither, but heated to dryness following a one hour exposure to the same immersion matrix. After this exposure all stents were baked at 380° C. Stents exposed to ultrasonic treatment displayed a 40% yield, while the yield of the refluxed stent was 30%, and the stent treated with the step of evaporation was variable form 10–30%. The stents that were ultrasonically treated exhibited much more uniformity in their radioisotope coating compared with stents that were loaded by heating to evaporation. Furthermore, it is noted that the rate of leaching of ultrasonically treated stents is 10 fold lower than those that were refluxed or heated to evaporation.

Effect of Baking

Precleaned stainless steel stents were immersed in aqueous form carrier-free Y-90 ($NH_4OH$) in a low volume on a heated surface (immersion matrix 50–60° C.) for 25 min. The resultant labelled stents were then rinsed with water, dried in a glass vial, and baked in an oven at 350° C. for 1 hour. After a number of repeated washings (heated saline and ultrasonic, as defined above), the stents were dried. The results are exhibited in FIG. 5.

Effect of Ultrasonic Treatment

Precleaned stainless steel stents were immersed in aqueous form Y-90 (ammonium) in a low volume on a heated surface (immersion matrix 50–60° C.) for 25 min, in the presence or absence of ultrasonic treatment. The stent that was not exposed to ultrasonic treatment was dried over a hot plate (200° C.). The resultant labelled stents were then rinsed with water, dried in a glass vial, and baked in an oven at 350° C. for 1 hour. After a number of repeated washings (saline/heat/ultrasonic, as defined above), the stents were dried. The results are exhibited in FIG. 6A.

Stents exposed to the step of ultrasonic treatment continued up to 170 µCi of affixed isotope with ±10% radial and longitudinal uniformity.

B) P-32

Effect of Cleaning Solution

Stainless steel stents were cleaned using either nitric or citric acids, and exposed to ultrasonic treatment for 1 hour at 50° C. within an ammonium nitrate immersion matrix containing carrier-free P-32. Stents cleaned with citric acid resulted in a 15% yield, while those cleaned with nitric acid demonstrated a 40% yield.

Another set of experiments were conducted with stainless steel stents cleaned with citric acid and either ultrasonically treated or refluxed for 1 hour within ammonium nitrate immersion matrix in the presence of carrier-free P-32, then baked at 380° C. for 1 hour. In either case the yield was 5%.

This indicates that the cleaning solution may have an effect on the interaction between the radioisotope and substrate. For further analysis, stents were cleaned with nitric acid.

Effect of Ultrasonic, Heating to Evaporation, or Reflux Treatments on Yield:

Stents were cleaned using nitric acid, and exposed to an ammonium nitrate immersion matrix (0.05 g ammonium nitrate to 0.5 g $H_2O$) and carrier-free P-32 in the presence or absence of ultrasonic exposure at 70° C. for 1 hour. Stents that were not exposed to ultrasonic treatment were either refluxed for 1 hour, or immersed at 70° C. for 1 hour prior to being dried over a hot plate (200° C.). All stents were baked at 350° C.

Stents that were refluxed or heated to evaporation resulted in a 10% yield, while those exposed to ultrasonic treatment resulted in a 20% yield. Furthermore, the uniformity of stents that were ultrasonically treated was much greater than those that were heated. Therefore, with all other parameters being held constant, ultrasonic treatment significantly increases the yield and uniformity of the coated substrate.

Figure 6B:
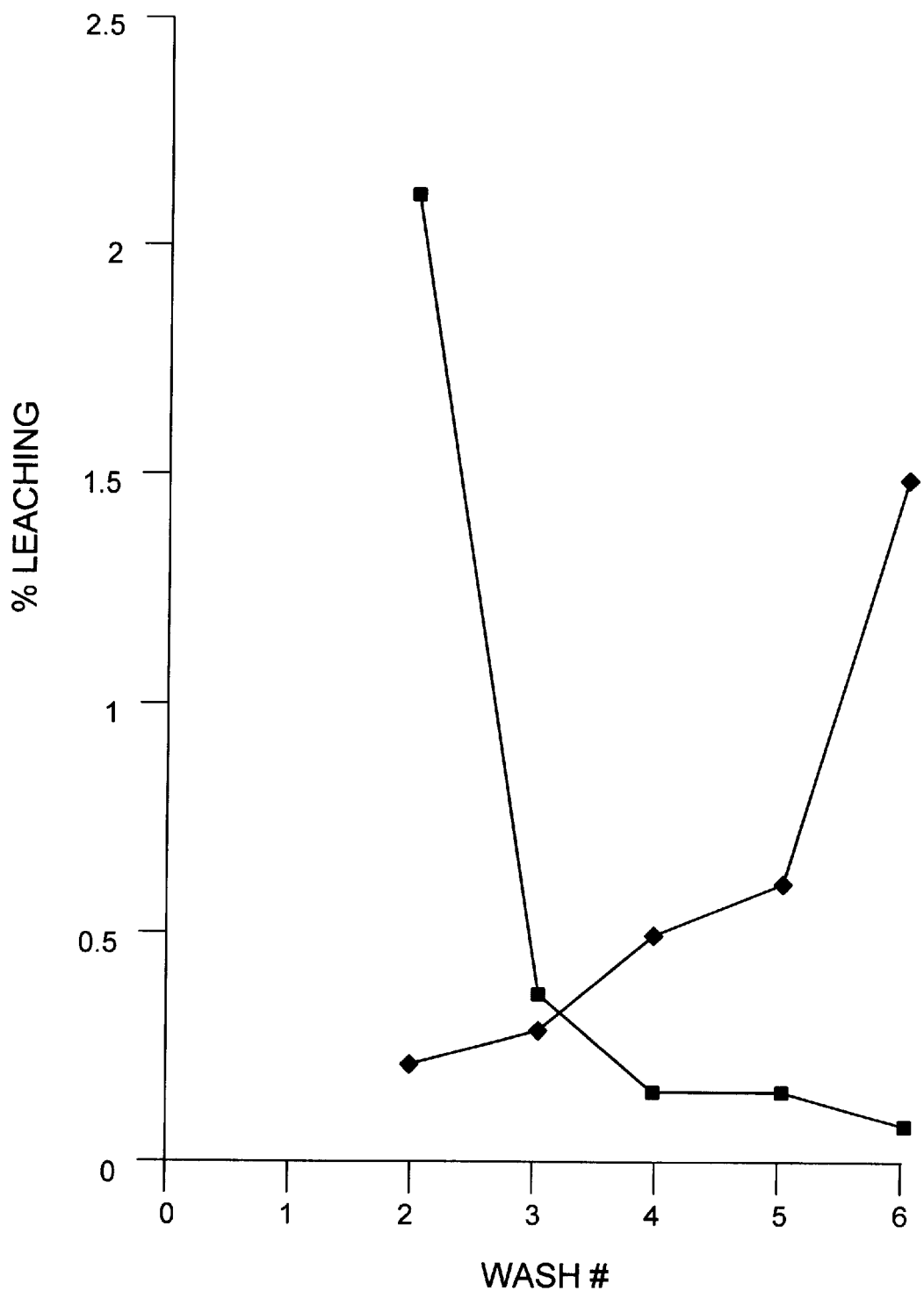

Effect of Ultrasonic Treatment v.s. Heating to Evaporation on Isotope Leaching:

Precleaned stents were immersed in aqueous form P-32 (carrier-free) in a low volume (0.5–1.5 ml) immersion matrix containing ammonium nitrate, and either exposed to ultrasonic vibration at 60–65° C. for 25 min, or left in the immersion matrix at the same temperature for the same length of time. The stents that were not exposed to ultrasonic treatment were placed onto a heated surface (about 200° C.) and evaporated to dryness. The resultant P-32 labelled stents were then rinsed with water (2 ml), and baked in an oven (at 350–380° C. for 1 hour). After a number of repeated washings, the stent was dried. The leaching rate for these stents is presented in FIG. 6B)

Another set of experiments were performed examining the length of ultrasonic treatment on yield, wherein stents were treated to either 1 or 2 hours of ultrasonic treatment in ammonium nitrate, and baked for 1 hour at 380° C. Stents exposed to 1 hour of treatment exhibited a 30% yield, while after 2 hours they displayed a 50% yield. In both cases the uniformity was ±8%. Therefore, exposure to ultrasonic treatment results in uniform radioisotope coatings, and longer treatments results in higher yields.

Effect of Baking:

Stainless steel stents were exposed to ultrasonic treatment in an ammonium nitrate immersion matrix for 25 min at 50–60° C. and treated as per the method of this invention except that some stents were not baked at 350° C. for 1 hour. Stents that were baked released 2.1, and 0.34% of the radioisotope in the first and second washes, while stents that were not baked released 9.5 and 0.76%, respectively.

C) Ag-110

Stainless steel stents were cleaned and exposed to ultrasonic treatment for 10 min at 50° C. within 0.1% $NaHCO_3$ containing Ag-110 (prepared via neutron bombardment of a silver target, i.e. not carrier free). Stents coated in this manner exhibited a 10% yield.

EXAMPLE 3

The antiproliferative effect of ionizing stents, prepared using the method of this invention, on restenosis was examined within pigs. Stents were implanted using standard protocols (see Carter et al 1996) for 1 or 3 month periods. Preliminary results indicate that the rate of leaching of the coated isotope from the stent in vivo is negligible, and well within medical standards. Furthermore, results indicate that these stents prevent restenosis and inhibit vascular constriction.

The present invention has been described with regard to preferred embodiments. However, it will be obvious to persons skilled in the art that a number of variations and modifications can be made without departing from the scope of the invention as described in.

All scientific publications and patent documents are incorporated herein by reference.

REFERENCES

Arlinghaus, H. F., Kwoka, M. N., Guo, X-Q. Multiplexed DNA Sequencing and Diagnositics by Hybridization with Enriched Stable Isotope Labels. Anal. Chem. vol 69. pp. 1510–1517 (1977).
Carter, A. J., Laird, J. R., Bailey, L. R., Hoopes, T. G., Farb, A., Fischell, D. R., Fischell, R. E., Fischell, T. A., Virmani, R. Effects of Endovascular Radiation from a B-particle-Emitting Stent in a Porcine Coronary Restenosis Model. Circulation vol 94. pp. 2364–2368 (1996).
Corbridge. Phosphorous, and Outline of its Chemistry, Biochemistry and Uses. The Studies in Inorganic Chemistry Series. No. 20. Elsevier, (1995)
Eichholz, G. G., Nagel, A. E., Hughes, R. B. Adsorption of Ions in Dilute Aqueous Solutions on Glass and Plastic Surfaces. Anal. Chem. Vol. 37, pp.863–868 (1965).
Fehsenfeld, P., Kleinraham, A., Schweikert, H. Radionuclide Technique in Mechanical Engineering in Germany. J. Radioanal. Nucl. Chem vol 160, pp. 141–151 (1991)
Fischell, T. A., Carter, A. J., Latro, J. R. The Beta-Particle-Emitting Radioisotope Stent (Isostent): Animal Studies and Planned Clinical Trials. Am J. Cardiol. vol 78 (suppl 3A), pp. 45–50 (1996).
Fischell T. A., Kharma, B. K., Fischell, D. R., Loges, P. G., Coffey II, C. W., Duggan, D. M., Naftilan A. J. Low-Dose, β-Particle Emission from 'Stent' Wire Results in Complete, Localized Inhibition of Smooth Muscle Cell Proliferation. Circulation vol 90, pp.2956–2963 (1994).
Hehrlein, C., Fehsenfeld, P. Radioactive Stents via Vascular Brachytherapy, Eds. Waksman, R., King, S. B., Crocker, I. B., Mould, R. F. Chap 21.(1996)
Hehrlein, C., Gollan, C., Donges, K., Metz, J., Riessen, R., Fehsenfeld, P., von Hodenberg, E, Kubler, W. Low Dose Radioactive Endovascular Stents Prevent Smooth Muscle Cell Proliferation and Neointimal Hyperplasia in Rabbits. Circulation vol 92, pp. 1570–1575, (1995).
Nickles, A. A., Kulago, B. R., Thomadsen, L. A., DeWerd, E. D., Werts, C. K., Stone. Making Radioactive Stents To Inhibit Restenosis Following PCTA. Proceedings of 44th Annual Meeting of Society of Nuclear Medicine, San Antonio, Tex., Jun. 1–5, (1997).
Wizemann, H. D., Niemax, K. Cancellation of Matrix Effects and Calibration by Isotope Dilution in Isotope-Selective DioideLaser Atomic Absorption Spectrometry. Annal Chem. vol 69. pp 4291–4293 (1997).
Wong, S. C., Leon, M. B. Intercoronary Stents. Curr. Opin. Cardiol. vol 10, pp. 404–411 (1995).
Violaris, A. G., Ozaki, Y., Serruys, P. W. Endovascular Stents: a 'break through technology', future challenges. Int. J. Cardiac Imaging vol 13, pp.3–13 (1997)

The embodiments of the invention in which an exclusive property of privilege is claimed are defined as follows:

1. A method for coating a substrate with a radioisotope comprising:
    a) immersing said substrate within a solution comprising an immersion matrix and containing a $\gamma$, $\beta^+$, $\alpha$ or $\beta^-$ emitting radioisotope;
    b) exposing said substrate to tuned vibrational cavitation to produce a coated substrate;
    c) baking said coated substrate at a temperature below the recrystallization temperature of said substrate;
    d) rinsing said coated substrate; and
    e) drying said coated substrate,
wherein said immersion matrix is not substantially retained on the surface of said substrate.

2. The method as claimed in claim 1, wherein said radioisotope is selected from the group consisting of non-metallic, metallic, rare earth and actinide radioactive isotopes.

3. The method as claimed in claim 2, wherein said non-metallic radioisotope includes: P-32, P-33, C-14, S-35, Cl-36, I-125, I-131, I-123 and I-124.

4. The method as claimed in claim 2, wherein said metallic radioisotope includes: Y-90, Pd-103, Pd-112, Co-55, Co-57, Co-60, Ag-110, Ag-111, Ag-112, Ag-113, Au-199, Cu-64, Re-186, Re-188, Ir-192, Ir-194, Mo-99, Ni-63, In-111 and Tc-99m.

5. The method as claimed in claim 2, wherein said rare earth radioisotope includes: Ho-166, Gd-159, and Pm-142.

6. The method as claimed in claim 2, wherein said actinide isotope is Am-241.

7. The method as claimed in claim 2, wherein said radioisotope is selected from P-32, Y-90, Ag-110, Ag-111, Ag-112 and Ag-113.

8. The method of claim 7 wherein said radioisotope is P-32.

9. The method of claim 7 wherein said radioisotope is Y-90.

10. The method claim 2 wherein the immersion matrix is buffered to about neutral pH.

11. The method of claim 10, wherein the coated substrate of step c) is baked at a temperature above 100° C.

12. The method of claim 11, wherein the coated substrate is baked at a temperature from about 250° to about 420° C.

13. The method of claim 1 wherein the rate of leaching of said isotope from said coated substrate of step d) is below 0.2% per 15 minutes.

14. The method of claim 1, wherein the steps of immersing, exposing, baking, rinsing and drying are automated.

15. The method of claim 1, wherein the substrate is a medical device.

16. The method of claim 1 wherein the tuned vibrational cavitation includes an ultrasonic bath.

17. The method of claim 1 wherein the tuned vibrational cavitation includes laser tuning.

18. The method as claimed in claim 10, wherein the immersion matrix is saline solution.

19. The method of claim 1 wherein said substrate is metallic.

20. The method of claim 1 wherein said substrate is non-metallic.

21. The method of claim 10 wherein the substrate is stainless steel.

22. The method of claim 10 wherein the substrate is glass.

23. The method of claim 10 wherein the substrate is plastic.

24. The method of claim 10 wherein the substrate is polytetrafluoroethylene.

25. The method of claim 1, wherein, in step:
   a) the substrate is immersed within a solution containing Y-90, $NH_4OH$ and EtOH;
   b) the immersed substrate of step a) is ultrasonically treated to produce a coated substrate;
   c) the coated substrate is baked at a temperature between from about 250 to 600° C.;
   d) the coated substrate is rinsed; and
   e) dried.

26. The method of claim 1, wherein, in step:
   a) the substrate is immersed within a solution containing P-32 and ammonium nitrate;
   b) the immersed substrate of step a) is ultrasonically treated to produce a coated substrate;
   c) the coated substrate is baked at a temperature between from about 250 to 600° C.;
   d) the coated substrate is rinsed; and
   e) dried.

27. The method of claim 15, wherein the medical device can comprise a variety of surface geometries, and is selected from the group consisting of: stent, expandable stent, delivery wire, catheter, seed, protheses, valves, and staples or other wound closure device.

28. The method of claim 27, wherein the medical device is a stent.

* * * * *